United States Patent [19]

Bourbon et al.

[11] Patent Number: 5,026,561

[45] Date of Patent: Jun. 25, 1991

[54] METHOD WHICH INHIBITS OR DESTROYS AT LEAST ONE UNICELLULOR LIVING ORGANISM CONTAINING A QUATERNARY AMMONIUM FLUORIDE

[75] Inventors: Pierre Bourbon, Toulouse, France; Pierre Lagny, Clebridge, Ireland; Pierre Billot, Neuilly Sur Seine, France

[73] Assignee: Atlantic Pharmaceutical Products Limited, Celbridge, Ireland

[21] Appl. No.: 246,878

[22] Filed: Sep. 20, 1988

[30] Foreign Application Priority Data

Sep. 23, 1987 [FR] France ............................ 87 13156
Nov. 23, 1987 [EP] European Pat. Off. ........ 87402632.1

[51] Int. Cl.$^5$ ...................... A61K 31/14; A61K 33/14
[52] U.S. Cl. ...................................... 424/673; 514/643
[58] Field of Search ........................... 424/673; 514/643

[56] References Cited

U.S. PATENT DOCUMENTS

| | | | |
|---|---|---|---|
| 3,647,700 | 3/1972 | Phillips | 252/89 |
| 3,995,029 | 11/1976 | Weisz | 424/151 |
| 3,996,350 | 12/1976 | Weisz | 424/151 |
| 4,097,590 | 6/1978 | Weisz | 424/151 |
| 4,206,233 | 6/1980 | Quinlan | 424/339 |
| 4,321,277 | 3/1980 | Saurino | 514/643 |
| 4,359,475 | 11/1982 | Walker | 424/273 R |
| 4,368,186 | 1/1983 | Vickery et al. | 424/78 |
| 4,473,547 | 9/1984 | Sipos | 424/152 |
| 4,490,353 | 12/1984 | Crawford et al. | 424/52 |

FOREIGN PATENT DOCUMENTS 0055109 12/1981 European Pat. Off. .
0162574 4/1985 European Pat. Off. .

Primary Examiner—Leonard Schenkman

[57] ABSTRACT

The invention relates to a method for inhibiting or destroying unicellular living organisms of a human or animal. The method comprises contacting the unicellular living organisms with the composition which comprises at least one quaternary ammonium salt and which may further comprises a metal fluoride for example, lithium fluoride. A preservative, such as Kathon (Registered Trademark) may also be present in the composition. The method is useful in inhibiting or destroying unicellular living organisms such as viruses or retroviruses, fungi, bacteria, or organisms which cause sexually transmittable diseases. The method may also be used to inhibit or destroy spermatozoa, or inhibit pathogenic microorganisms.

44 Claims, No Drawings

METHOD WHICH INHIBITS OR DESTROYS AT LEAST ONE UNICELLULOR LIVING ORGANISM CONTAINING A QUATERNARY AMMONIUM FLUORIDE

BACKGROUND OF THE INVENTION

The invention relates to the inhibition or destruction of unicellular living organisms such as protozoa, microbes, bacteria, gametes, fungi, yeasts or the like, and viruses. It relates, more especially, to the technical fields of local contraception, of antibiotic therapy, of antisepsis, of combating sexually transmitted diseases including mycoses, and of combating viral conditions, in the context of pharmacy for human or veterinary use or of cosmetics. The invention may also be advantageously applied in the field of the disinfection of surfaces or alternatively in agriculture, for example in combating fungi and bacteria.

Many substances that inhibit or destroy unicellular living organisms are already known, and these include surfactant agents such as quaternary ammonium salts. In particular, it is known that quaternary ammonium halides such as benzalkonium chloride (or dimethylbenzylammonium chloride), alone or in combination with other active principles, are advantageous in these applications (see, for example, British Patent No. 1,554,615, French Patent Nos. 2,431,859, 2,483,177, 2,379,508, 2,384,497, 2,457,641, 2,573,624, 2,418,221, 2,562,888, European Patent Nos. 0,243,713, 0,175,338, 0,132,963, 0,127,131, 0,094,562, 0,076,136, 0,068,399, 0,037,593, unpublished European Patent Application No. 86/402,716.4, filed on 8.12.1986, and international applications WO No. 84/00,877 and WO No. 84/02,649).

It is also known, moreover, that the quaternary ammonium halides which are the easiest to manufacture and the best known, for these applications and in other known applications, are the chlorides, iodides, bromides and chloroiodites (see patents mentioned above, and also French Patent Nos. 2,002,945, 2,185,717, 2,267,092, 2,366,260, 2,366,261, 2,391,991, 2,418,220, 2,419,024, 2,482,090, 2,505,325, 2,517,672, 2,562,799 and European Patent No. 0,191,236).

Moreover, the prior art has already provided many processes for manufacturing these quaternary ammonium salts, but which are directly applicable, among quaternary ammonium halides, only to the chlorites and/or iodides and/or bromides and/or chloroiodites (see above patents and also French Patent Nos. 2,472,558, 2,033,044 and European Patent Nos. 0,094,552 and 0,012,296).

Ammonium fluoride, and processes for preparing and purifying it, are also known (see, for example, French Patent Nos. 2,244,713, 2,253,710 and European Patent No. 0,002,016), as are perfluorinated or polyfluorinated quaternary ammonium salts (for example, French Patent Nos. 2,038,421, 2,051,095, 2,153,489 and European Patent Nos. 0,073,760, 0,100,478, 0,100,477, 0,149,172).

Ionic fluorine is, moreover, well known for its anti caries properties in dental applications (for example, U.S. Pat. No. 4,473,547; VIDAL dictionary, 1985, page 582, O.V.P., Paris, "fluor monal"), optionally combined with a cationic quaternary ammonium compound (see French Patent Nos. 1,486,676 and 1,297,708). In these latter documents, the advantages demonstrated of combining, in one and the same compound, on the one hand fluorine, well known for its anti caries properties, and on the other hand surfactant quaternary ammonium salts, known for their bactericidal properties. However, no genuinely synergistic activity is demonstrated in these applications for dentifrices, with the quaternary ammonium fluorides tested, either with respect to anti caries properties or with respect to bactericidal properties.

French Patent No. 1,297,708 describes, in particular, laurylbenzyldimethylammonium fluoride, a process for preparing this fluoride and its application in a toothpaste. This patent teaches the bactericidal effect of the quaternary ammonium compound and the anti caries effect of the fluorine. However, no synergy is demonstrated between the fluorine and the quaternary ammonium compound.

Finally, Italian Patent No. 1,153,530 describes a process for preparing quaternary ammonium carbonates and then, from these carbonates, quaternary ammonium halides by anion exchange with the corresponding acid, which is stronger than carbonic acid. However, this patent does not mention how this process can be applied to the preparation of fluorides. Moreover, while the compounds obtained by means of this process are suitable for application in the disinfection of surfaces and in industry, they cannot be used directly on human beings or animals, for example in the pharmaceutical compositions in which the compounds must be of high purity.

With respect to this general state of the art, the invention raises the problem of providing a composition that completely inhibits or destroys unicellular living organisms and which is simultaneously applicable to living organisms, human, animal or plant, without thereby causing harmful side effects. In effect, it is difficult, or even impossible, to prepare such a composition at the present time using quaternary ammonium halides without being reconciled either to producing side effects (irritations, allergies, red blotches, etc.) or to being insufficiently active. The problem arises especially with known spermicidal compositions based on benzalkonium chloride, or in combating viruses or retroviruses such as herpes or the LAV, responsible for AIDS.

The invention relates, in particular, to improving the invention which is the subject of unpublished European Patent Application No. 86/402,716.4 and U.S. patent application Ser. No. 07/053 374 filed on May 22 1987 by the applicant.

SUMMARY OF THE INVENTION

The inventors have demonstrated that, among known quaternary ammonium halides, the benzalkonium fluoride of general formula:

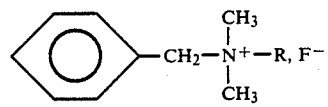

where R is an alkyl radical which can vary between C8H17 and C18H37, provides a markedly better and unexpected activity in the field of the destruction or inhibition of unicellular living organisms.

In particular, the results are markedly better than could have been expected on the basis of the known respective properties of ionic fluorine and of the benzalkonium cation, in particular those stated in unpublished European Patent Application No. 86/402,716.4 and U.S. patent application Ser. No. 07/053 374 or in French Patent No. 1,297,708.

The invention relates to a composition that inhibits or destroys at least one unicellular living organism, protozoan, microbe, fungus, yeast, virus or the like, and more especially an antibiotic composition, a virucidal composition, a fungicidal composition, a bactericidal pharmaceutical composition, a composition intended for application on the genital organs in order to combat sexually transmitted diseases, a local contraceptive composition, in particular a spermicidal composition, a cosmetic composition or composition for body hygiene, or a composition for the local disinfection of the human body or of surfaces, characterized in that it contains at least one benzalkonium fluoride as defined above. Preferably, the radical R is an alkyl radical between $C_{12}H_{25}$ and $C_{14}H_{29}$. More especially, the invention relates to a galenical composition, characterized in that it contains between 0.05% and 7% by weight, in particular of the order of 1%, of a benzalkonium fluoride of this kind, sufficiently purified so as to be usable for human beings or animals.

A composition according to the invention can contain another active principle, chosen in accordance with the purpose for which the composition is intended—in particular an antibiotic—in combination with the abovementioned benzalkonium fluoride.

Similarly, a composition according to the invention advantageously contains, in addition to the abovementioned benzalkonium fluoride, at least one metal fluoride. The proportions of benzalkonium fluoride and of metal fluoride to be used enable the proportion of ionic fluorine $F^-$ to be varied relative to the proportion of benzalkonium. A composition according to the invention preferably contains lithium fluoride, which has proved to have a surprising additional synergistic effect.

The invention relates to such a composition characterized in that it contains one and only one quaternary ammonium halide which formula corresponds to the above mentioned formula.

More generally, the invention relates to a medicinal product, characterized in that it contains at least one benzalkonium fluoride as mentioned above. The radical R is preferably an alkyl radical between $C_{12}H_{25}$ and $C_{14}H_{29}$, and the benzalkonium fluoride is preferably present in a proportion varying between 0.2% and 1% by weight.

The invention also relates to the application of at least one quaternary ammonium fluoride of general formula $R_1 R_2 R_3 RN^+ F^-$ for obtaining a composition according to the invention, and more especially a spermicidal composition, an antibiotic pharmaceutical composition that can be administered systemically, an antibiotic topical composition, a bactericidal pharmaceutical composition, a topical composition intended for combating viral conditions, in particular viral conditions of the skin and the genital organs, a pharmaceutical composition that can be administered systemically or parenterally intended for combating viruses or retroviruses, in particular herpes or the LAV (or HIV) responsible for AIDS, or a composition intended for combating fungal conditions. Preferably, the radical R1 is composed of a benzyl radical, $R_2$ and $R_3$ are composed of a methyl radical and R is an alkyl radical between $C_8H_{17}$ and $C_{18}H_{37}$, so that the quaternary ammonium fluoride referred to is a benzalkonium fluoride as mentioned above. More especially, R is preferably an alkyl radical varying between $C_{12}H_{25}$ and $C_{14}H_{29}$.

The invention also relates to a process for preparing a quaternary ammonium fluoride in the form of a solid or pasty salt that is sufficiently pure to be included in a composition intended for human beings or animals, characterized in that a quaternary ammonium methyl carbonate is reacted in stoichiometric amounts with hydrofluoric acid solubilized in an alcohol, until the gaseous evolution of carbon dioxide has ceased, and the remaining alcohol is then removed by evaporation under vacuum. Preferably, the quaternary ammonium methyl carbonate is purified beforehand by washing it in the heated state in petroleum ether until its amber yellow colour has disappeared, and the quaternary ammonium methyl carbonate is then separated off after settling has taken place. The hydrofluoric acid solubilized in an alcohol is obtained by the displacement of gaseous hydrofluoric acid with a stream of air from a 40% strength aqueous solution, and solubilization in the alcohol at 0° C. Preferably, the hydrofluoric acid is solubilized in methanol. The evaporation of the alcohol under vacuum is preferably carried out in two stages, in particular a stage under a pressure of 10 mm of mercury $(1.333224 \times 10^3 Pa)$ followed by a stage under a pressure of 0.01 mm of mercury (1.33224 Pa). The quaternary ammonium fluoride obtained is subsequently purified by washing in the heated state in petroleum ether, followed by separation by centrifugation and drying under vacuum. It is also possible to purify the quaternary ammonium fluoride obtained by dissolution in the heated state in acetone, followed by slow cooling, separation of the pasty residue and drying under vacuum. The preparation process of the invention is advantageously applicable to the preparation of a benzalkonium fluoride as mentioned above. It enables an extremely pure salt to be obtained, which is usable in a composition intended for human beings or animals, in particular a pharmaceutical composition. The benzalkonium methyl carbonate used together with the hydrofluoric acid may be obtained as taught in Italian Patent No. 1,153,530, from the corresponding tertiary amine and dimethyl carbonate.

EXAMPLES AND PREFERRED EMBODIMENTS

Example of Preparation of a C1 Benzalkonium Fluoride

Three kilogrammes of C12 dimethylbenzylammonium methyl carbonate are treated with 6.3 l of 1.25N HF solubilized in methanol.

A strong evolution of carbon dioxide takes place. At the end of the reaction, the pH is between 5 and 6. After evaporation of the methanol under vacuum, an amber yellow translucent pasty mass is obtained.

The purification of this pasty mass is performed by dissolution in the heated state of the translucent mass in acetone in the heated state. After slow cooling, the pasty residue is separated off and then freed from the remaining solvent under vacuum.

The purity of the benzalkonium fluoride obtained is monitored by an assay of the F ions with a specific electrode, and an HPLC (high pressure liquid chromatography) assay of the quaternary ammonium. In this example, the purity of the product obtained was 99%.

Example of Preparation of a $C_{12}$ Benzalkonium Fluoride with Prior Purification One kilogram of $C_{12}$ dimethylbenzylammonium methyl carbonate brought to its melting point is washed with petroleum ether and dried under vacuum.

It is then attacked in the molten state with 2.76 l of 1.5N HF in methanol. A strong evolution of carbon dioxide takes place. At the end of the reaction, the pH is between 5 and 6. After evaporation of the methanol under vacuum, an amber yellow translucent pasty mass is obtained. The purification is performed by dissolution in the heated state of the translucent mass in acetone in the heated state. After slow cooling, the pasty residue is separated off, and then freed of the remaining solvent under vacuum.

The purity of the product, monitored according to the same method as in the previous example, was 99%.

Example of Preparation of a C14 Benzalkonium Fluoride

The same processes of manufacture as in the 2 previous examples were used, substituting C14 dimethylbenzylammonium methyl carbonate for $C_{12}$ dimethylbenzylammonium methyl carbonate.

The benzalkonium fluoride obtained also takes the form of an amber yellow pasty mass.

After purification, the purity was 98% and 99%, respectively.

The benzalkonium fluorides prepared as described above were used in the trials described below, enabling their activity to be measured.

Except where otherwise stated, the methodologies employed were those already described in European Patent Application No. 86/402,416.4, filed on 8.12.1986 and U.S. patent application Ser. No. 07/053 374 filed on 22.05.1987 by the applicant. The teaching of these European and U.S. patent applications is considered to be known and integrated in the description below.

Trial No. 1: Spermicidal Activity of the Compositions in Vitro

The SANDERS CRAMER tests, according to IPPF (International Planned Parenthood Federation) standards, were carried out in order to determine the minimal inhibitory concentration of benzalkonium fluoride. A minimal inhibitory concentration (MIC) of $C_{12}$ benzalkonium fluoride of 20 mg/l, equivalent to 0.002%, was thereby obtained. This value is to be compared with the MIC of benzalkonium chloride alone, which is 0.063%, and with the MIC of benzalkonium chloride in the presence of $F^-$ anions at a concentration of 1 μg/ml, which is 0.003%. As is hence observed, benzalkonium fluoride procures a higher activity than benzalkonium chloride alone, and also a higher activity than the combination of benzalkonium chloride with fluoride anions $F^-$, for example in the form of sodium fluoride.

Under the same conditions, benzalkonium fluoride in the presence of sodium fluoride at a concentration of 1 mg/l has an MIC of 18 mg/l, equivalent to 0.0018%. This MIC falls to 15 mg/l, equivalent to 0.0015%, in the presence of lithium fluoride at a concentration of 1 mg/l.

Trial No. 2: Activities of Spermicidal Galenical Preparations Compared

This in vitro trial was carried out on galenical preparations containing, as active principle, either benzalkonium chloride alone, or benzalkonium chloride with 0.45% by weight of fluoride anions $F^-$ in the form of sodium fluoride, or benzalkonium fluoride. The MIC values are determined after in vitro simulation of the true in vivo conditions (extraction, solubilization, etc.). The SANDERS CRAMER test of the IPPF is then carried out in vitro. The results obtained are summarized in the following tables:

| GALENICAL FORM | Proportion of benzalkonium choloride alone (by weight) in the galenical form | MIC (% by wt.) of benzalkonium chloride |
|---|---|---|
| Pessary | 1.2% | 0.0063% |
| Cream | 1.2% | 0.0083% |
| Tablet | 1.2% | 0.0075% |
| Soluble film | 3.12% | 0.0095% |
| Jelly | 1.2% | 0.0080% |

| GALENICAL FORM | Proportion of benzalkonium chloride (by weight) in the galenical form with 0.45% of $F^-$ anions | MIC (% by wt.) of benzalkonium chloride |
|---|---|---|
| Pessary | 1.2% | 0.0023% |
| Cream | 1.2% | 0.0030% |
| Pad | 1.2% | 0.0025% |
| Tablet | 3.12% | 0.0025% |
| Soluble film | 1.2% | 0.0017% |
| Jelly | 1.2% | 0.0033% |

| GALENICAL FORM | Proportion of benzalkonium fluoride alone (by weight) in the galenical form | MIC (% by wt.) of benzalkonium fluoride |
|---|---|---|
| Pessary | 1% | 0.0019% |
| Cream | 1% | 0.0022% |
| Pad | 1% | 0.0020% |
| Tablet | 2.5% | 0.0020% |
| Soluble film | 1% | 0.0012% |
| Jelly | 1% | 0.0026% |

It is hence observed that benzalkonium fluoride has a minimal inhibitory concentration which is very much lower than that of benzalkonium chloride, and even than that of benzalkonium chloride in the presence of $F^-$ anions. A surprising synergistic effect is hence due to the benzalkonium fluoride.

Trial No. 3: Fungicidal Activities Compared

The fungicidal activities were tested on three strains of mould according to AFNOR Standard T72-201. The three strains of mould were as follows:

*Aspergillus versicolor* CNCM 1187-79,
*Cladosporium cladosporioides* CNCM 1185-79,
*Penicillium virrucosum* variety *cylopium* CNCM 1186-79.

The trial was also carried out on a strain of yeast: *Candida albicans* (ATCC 2091) CNCM 1180-79.

The trials were carried out with a contact time of 15 min. at 20° C. Two types of trials were carried out: a first trial comparing the fungicidal activity of benzalkonium chloride alone with benzalkonium fluoride alone, and a second trial comparing the fungicidal activity of benzalkonium chloride combined with lithium fluoride and the preservative KATHON (registered trademark) with the fungicidal activity of benzalkonium fluoride combined with lithium fluoride and the same preservative KATHON (registered trademark).

KATHON (registered trademark) is a known preservative marketed by RHOM AND HASS COMPANY (U.S.A.), consisting of a mixture of two isothiazolines: 5-chloro-2-methyl 4-isothiazolin-3-one and 2-methyl-4-isothiazolin-3-one (IUPAC nomenclature).

The results are summarized in the following tables:

| | Fungicide concentration according to AFNOR standard in µg/ml (ppm) | |
|---|---|---|
| | Benzalkonium chloride | Benzalkonium fluoride |
| Aspergillus versicolor | 100 | 100 |
| Cladosporium | 200 | 200 |
| Penicillium | 50 | 50 |
| Candida Albicans | 50 | 50 |

| | Fungicide concentration according to AFNOR standard in µg/ml (ppm) | |
|---|---|---|
| | Benzalkonium chloride + LiF 0.96 µg/ml + KATHON ® 0.49 µg/ml | Benzalkonium fluoride + LiF 0.96 µg/ml + KATHON ® 0.49 µg/ml |
| Aspergillus versicolor | 100 | 100 |
| Cladosporium | 2000 | 100 |
| Penicillium | 50 | 50 |
| Candida Albicans | 50 | 50 |

It is hence observed that the combination of benzalkonium fluoride with lithium fluoride and the preservative KATHON (registered trademark) is, in some cases, better than the combination of benzalkonium chloride with lithium fluoride and the same preservative KATHON (registered trademark).

The activity of benzalkonium chloride and benzalkonium fluoride, alone or in the presence of lithium fluoride at a concentration of 0.96 mg/l, was tested on wild-type strains of *Aspergillus niger* originating from hospital sources. The results are as follows:

| | Fungicide concentration in mg/l |
|---|---|
| Benzalkonium chloride alone | 150 |
| Benzalkonium chloride + LiF at 0.96 mg/l | 135 |

| | Fungicide concentration in mg/l |
|---|---|
| Benzalkonium fluoride alone | 115 |
| Benzalkonium fluoride + LiF at 0.96 mg/l | 100 |

Trial No. 4: Activity with Respect to the Pathogenic Organisms Responsible for Sexually Transmitted Diseases Trials were carried out on strains of Gonococcus, Trichomonas, Chlamydia, Gardnerella and Ducrey's bacillus.

The results obtained are summarized in the following table:

| STRAIN | Minimal inhibitory concentration (MIC) Benzalkonium chloride alone | Minimal inhibitory concentration (MIC) Benzalkonium chloride + F$^-$ 1 microgram/ml | Minimal inhibitory concentration (MIC) Benzalkonium fluoride |
|---|---|---|---|
| Gonoccus | 1.15 mg/liter | 0.60 mg/liter | 0.44 mg/liter |
| Trichomonas | 1.3 mg/liter | 0.90 mg/liter | 0.7 mg/liter |
| Chlamydia | 100 mg/liter | 85 mg/liter | 69 mg/liter |
| Gardnerella | 50 mg/liter | 41 mg/liter | 32.4 mg/liter |
| Ducrey's bacillus | 75 mg/liter | 62 mg/liter | 50.5 mg/liter |

A very strong decrease in the minimal inhibitory concentration is hence observed for benzalkonium fluoride.

Trial No. 5: Bactericidal Activity with Respect to Standardized Strains

This trial was performed according to AFNOR Standard NFT 72-150, March 1981. The neutralizing agent used was as follows: 3% of Tween 80 (V/V) and 0.3% of lecithin (M/V). The pH of the medium was 7.2. The results obtained are summarized in the following table:

| STRAIN | Minimal inhibitory concentration (MIC) Benzalkonium chloride | Minimal inhibitory concentration (MIC) Benzalkonium chloride + F$^-$ 1 microgram/ml | Minimal inhibitory concentration (MIC) Benzalkonium fluoride |
|---|---|---|---|
| *Pseudomonas aeruginosa* CNCM A 22 | 31.25 mg/liter | 18 mg/liter | 14.2 mg/liter |
| *Escherichia coli* CNCM 54 127 | 6.57 mg/liter | 3 mg/liter | 2.5 mg/liter |
| *Staphyloccocus aureus* Oxford strain CNCM 53 154 | 1.56 mg/liter | 1.1 mg/liter | 1.1 mg/liter |
| *Staphyloccocus faecalis* | 4 mg/liter | 3.6 mg/liter | 2.9 mg/liter |

-continued

| STRAIN | Minimal inhibitory concentration (MIC) Benzalkonium chloride | Minimal inhibitory concentration (MIC) Benzalkonium chloride + $F^-$ 1 microgram/ml | Minimal inhibitory concentration (MIC) Benzalkonium fluoride |
|---|---|---|---|
| CNCM 5 855 *Mycobacterium smegmatis* CNCM 7 326 | 30 mg/liter | 26 mg/liter | 21.9 mg/liter |

In this case also, a marked improvement is observed for benzalkonium fluoride.

Trial No. 6

The activity of benzalkonium chloride and benzalkonium fluoride, alone or in the presence of lithium fluoride at a concentration of 0.96 mg/l, or in the presence of lithium fluoride at a concentration of 0.96 mg/l and KATHON (registered trademark) preservative at a concentration of 0.47 mg/l, was tested on 80 wild-type strains of multi-resistant Escherichia coli producing plasmid 8-lactamase.

The MIC was determined in accordance with the methodology described by Profssors F. CATALAN, P. SEDNAOUI, A. MILOVANOVIC et al., Institut A. FOURNIER, Paris.

The results are as follows:

|  | MIC (in mg/l) |
|---|---|
| Benzalkonium chloride alone | 8 to 12 |
| Benzalkonium chloride + LiF at 0.96 mg/l | 6 to 9 |
| Benzalkonium chloride + LiF at 0.96 mg/l + KATHON ® at 0.47 mg/l | 4 to 6 |
| Benzalkonium fluoride alone | 4 to 8 |
| Benzalkonium fluoride + LiF at 0.96 mg/l | 4 to 6 |
| Benzalkonium fluoride + LiF at 0.96 mg/l + KATHON ® at 0.47 mg/l | 2 to 5 |

Trial No. 7

The resistance of Pseudomonas aeruginosa to various reputedly bactericidal active principles or commercial antiseptics was studied in terms of the hardness of the water and the presence or absence of proteins. The same trial was carried out on pure benzalkonium fluoride.

The methodology employed is that defined by AFNOR Standard T72-150, using the products diluted in accordance with the manufacturers' recommendations as regards the concentrations and conditions of use.

Mercryl Laurylé is a foaming solution marketed by Laboratoires LABAZ (Paris, France).

Cresol is the name given to three isomeric phenols, ortho, meta and para, $C_7H_8O$, and immediate homologues of phenol, HO—$C_6H_4$—$CH_3$.

Solubacter is a registered trademark denoting a foaming solution marketed by Laboratoire INNOTHERA (Arcueil, France).

Hibisprint is an alcohol solution marketed by ICI PHARMA (Cergy, France).

Cetavlon is an antiseptic solution marketed by ICI PHARMA (Cergy, France).

Hexomedine is a registered trademark denoting a non foaming solution marketed by THERAPLIX S.A. (Paris, France).

In the following table, R denotes resistance (a growth of colonies was observed), S denotes sensitive (no significant growth of colonies was observed), P+ means that proteins were added to the solvent, and P— means that the solvent does not contain proteins.

| ANTISEPTIC PRODUCTS TESTED | 0.2 ml of innoculum Contact time 10 min | | | | 0.4 ml of innoculum Contact time 20 min | | | | 0.6 ml of innoculum Contact time 30 min | | | |
|---|---|---|---|---|---|---|---|---|---|---|---|---|
|  | Distilled water | | Hard water | | Distilled water | | Hard water | | Distilled water | | Hard water | |
|  | P+ | P— | P+ | P— | P+ | P— | P+ | P— | P+ | P— | P+ | P— |
| Crude cresol | S | S | S | S | R | S | S | R | R | R | R | R |
| Mercryl Lauryle | R | S | R | R | R | R | R | R | R | R | R | R |
| Solubacter ® | S | S | R | S | R | R | R | R | R | R | R | R |
| Formaldehyde | S | S | S | S | S | S | S | S | S | S | S | S |
| Hexomedine ® | S | S | S | S | R | S | R | R | R | S | R | R |
| Hibisprint | S | S | S | S | S | S | R | R | R | R | R | R |
| Cetavlon | S | S | R | S | S | S | S | S | S | S | S | S |
| Zinc sulphate | R | R | R | R | R | R | R | R | R | R | R | R |
| Benzalkonium fluoride | S | S | S | S | S | S | S | S | S | S | S | S |

Trial No. 8: Virucidal Activity

This trial was carried out according to the method of gelfiltration on SEPHADEX LH 20.

The antiseptics used were $C_{14}$ benzalkonium chloride as powder, $C_{12}$ benzalkonium fluoride as crystals and lithium fluoride as powder. Dilution series in a geometric ratio of 2 were prepared in sterile double distilled water, and the trials were performed with 10, 30, 50, 80, 100, 200 and 500 mg/liter of benzalkonium chloride and benzalkonium fluoride, with or without the addition of lithium fluoride at a concentration of 1 or 1.70 mg/liter.

The cell cultures employed are VERO cells (strains ATCC CCL81), maintained on DMEM medium (EUROBIO), to which 5% of foetal calf serum and antibiotics (streptomycin at 50 microgramme per milliliter and penicillin at 200,000 $\mu$/l) were added.

The test virus was SABIN type 1 polio virus. It was cultured on VERO cells in ROUX dishes. The determination of the infectious titre was carried out according to the method of REED and MUENCH, using the conversion table of WYSHAK and DETRE.

The trial was carried out in three stages with, in the first place, the determination of the threshold of cytotoxicity of the antiseptics, then the study of the capacity of the cells treated with the antiseptics to develop the infection, and finally the determination of the virucidal effects of these antiseptics.

1—Determination of the Threshold of Cytotoxicity of the Antiseptics

Before any investigation of the virucidal effects, it is necessary to investigate the dilution of antiseptics responsible for a cytotoxic activity, before and after filtration.

Before filtration, the VERO cells are cultured on 96-well microfiltration plates. The antiseptics are then arranged in an increasing dilution at a geometric ratio on the basis of 0.1 ml per depression and 8 depressions per dilution on the cell lawns. The cells and the dilutions of virucidal substances are left in contact for one hour at 37° C., and the antiseptic substances are then removed and replaced by the culture medium without serum. It is then possible to calculate the LD0 (dilution of antiseptics not adversely affecting the cultured cells) after a 48-hour incubation.

30 ml of the suspension of SEPHADEX LH 20 gel are introduced into the filtration apparatus. This operation is followed by a centrifugation, and the solution of antiseptic is then deposited on the basis of 2 ml on the SEPHADEX column. A further centrifugation is carried out before the determination of the $LD_0$.

2—Capacity of the Cells Treated with Antiseptic to Develop the Viral Infection

VERO cells are cultured on 96-well microplates. The antiseptic is employed at its $LD_0$ and left in contact for one hour, and is then replaced by increasing 10-fold dilutions of polio virus. After one hour's contact, the viral suspension is removed and replaced by a culture medium without serum. The measurement of the cytopathic effect is made after a 48-hour incubation at 37° C.

3—Determination of the Virucidal Activity of the Antiseptics

All the doses of the antiseptics used are, obviously, less than the threshold of cytotoxicity recorded above. From the mixtures containing an equal volume of viral suspension and antiseptic, 1 ml is withdrawn at 30, 60, 120 and 180 minutes. The samples are then deposited on SEPHADEX columns, after which they are centrifuged. In parallel, a control viral suspension without antiseptic is processed under the same conditions.

The results are given in the following tables:
BKC: Benzalkonium chloride
BKF: Benzalkonium fluoride
LiF: Lithium fluoride

| Study of threshold of cytoxicity (LDO) | | |
|---|---|---|
| Antiseptic | Before filtration | After filtration |
| BKC | 0.05% | 0.01% |
| BKC + LiF | 0.05% | 0.01% |
| BKF | 0.01% | 0.005% |
| BKF + LiF | 0.01% | 0.005% |

| Capacity of the cells to develop the viral infection | | | | |
|---|---|---|---|---|
| | Titer of the viral suspensions (PFU/ml) | | | |
| Control virus | BKC + virus | °BKC + LiF§ + virus | BKF + virus | °BKF + LiF§ + virus |
| $10^{7.94}$ | $10^{7.84}$ | $10^{7.84}$ | $10^{6.84}$ | $10^{6.04}$ |

PFU = plaqueforming unit (PFU/ml)

| Virucidal activity of the antiseptics with respect to poliomyelitis virus after gel filtration, in terms of the contact time | | | | | |
|---|---|---|---|---|---|
| Antiseptic | Final concentration (in mg/l) | Viral titer expressed in PFU/ml virus/antiseptic contact time | | | |
| | | 30 min | 60 min | 120 min | 180 min |
| Benzalkonium chloride | 200 | $10^{1.74}$ | $10^{1.74}$ | $10^{1.74}$ | $10^{1.64}$ |
| | 100 | 0 | 0 | 0 | 0 |
| | 50 | $10^{1.74}$ | $10^{1.74}$ | $10^{1.64}$ | 0 |
| | 20 | $10^{1.84}$ | $10^{1.84}$ | $10^{1.74}$ | 0 |
| | 10 | $10^{4.84}$ | $10^{3.84}$ | $10^{3.84}$ | $\approx 0$ |
| Benzalkonium chloride + Lithium fluoride (1 mg/l) | 200 | $10^{1.84}$ | $10^{1.84}$ | $10^{1.74}$ | $10^{1.74}$ |
| | 100 | 0 | 0 | 0 | 0 |
| | 50 | $10^{1.84}$ | $10^{1.84}$ | $10^{1.84}$ | 0 |
| | 20 | $10^{1.74}$ | $10^{1.84}$ | $10^{1.64}$ | 0 |
| | 10 | $10^{3.84}$ | $10^{3.84}$ | $10^{3}$ | 0 |
| Benzalkonium fluoride | 200 | $10^{1.74}$ | $10^{1.74}$ | $10^{1.64}$ | $10^{1.84}$ |
| | 100 | 0 | 0 | 0 | 0 |
| | 50 | $10^{1.34}$ | $10^{1.34}$ | 0 | 0 |
| | 20 | $10^{1.64}$ | $10^{1.64}$ | $10^{1.64}$ | 0 |
| | 10 | $10^{2.54}$ | $10^{2.54}$ | $10^{2.34}$ | $10^{2.34}$ |
| Benzalkonium fluoride + Lithium fluoride (1 mg/l) | 200 | $10^{1.74}$ | $10^{1.74}$ | $10^{1.84}$ | $10^{1.84}$ |
| | 100 | 0 | 0 | 0 | 0 |
| | 50 | $10^{1.3}$ | $10^{1.3}$ | 0 | 0 |
| | 20 | $10^{1.84}$ | $10^{1.74}$ | $10^{1.34}$ | 0 |
| | 10 | $10^{3.84}$ | $10^{3.84}$ | $10^{3}$ | $10^{8.54}$ |

The virucidal activity in terms of the virus/antiseptic contact time hence shows that, for all the concentrations employed, the result obtained, that is to say the viral inhibition, is equal to or better than that required by the Environmental Protection Agency (see SS. BLOCK, "Disinfection, sterilization and preservation" Editions Lea and Febiger, Philadelphia U.S.A., 1977).

Benzalkonium chloride is active at a concentration of 0.01% in 30 minutes' contact. The same applies to benzalkonium fluoride. However, with lower concentrations, such as 0.0085% and 0.0082%, viral inhibition is noted from 120 minutes onwards with benzalkonium fluoride, whereas it is necessary to wait at least 180 minutes in the case of benzalkonium chloride.

Trial No. 9: Virucidal Activity According to the AFNOR Standard

The virucidal activity of benzalkonium fluoride was determined following AFNOR Standard T72-180. The following results were obtained:

(1) On type 2 herpes simplex virus:

| | Inhibitory concentration (% by weight) | Cell Toxicity |
|---|---|---|
| Benzalkonium chloride | 0.01% | 0.05% |
| Benzalkonium fluoride | 0.0075% | 0.08% |

(2) On cytomegalo virus:

| | Inhibitory concentration (% by weight) | Cell toxicity |
|---|---|---|
| Benzalkonium chloride | 0.01% | 0.05% |
| Benzalkonium fluoride | 0.0075% | 0.05% |

The preferred galenical forms of the invention for its applications in local contraception are as follows:

Pessaries
Benzalkonium fluoride: 1.00%
Excipients: semi-synthetic glycerides or cocoa butter, or gelatin, glycerin and purified water, antioxidants, antiseptics.

Creams
Benzalkonium fluoride: 1.00%
Excipients: distilled or purified water, humectants, gelling agents, emulsifier, stabilizer, antioxidant, antiseptic. (To be distributed in variable proportions according to the viscosity.) pH between 4.5 and 6.5 (preferably citric acid).

Ointments and salves
Benzalkonium fluoride: 1.00%
Excipients: distilled or purified water, emulsifier, excipients of the fatty type (vaseline, lanolin, lanovaseline, stearovaseline), stabilizer, antioxidant, antiseptic. (To be distributed in variable proportions according to the viscosity.) pH between 4.5 and 6.5 (preferably citric acid).

Jelly
Benzalkonium fluoride: 1.00%
Excipients: soluble derivatives of cellulose that are compatible with cationic surfactant detergents, distilled or purified water, glycerin, sorbitol, antioxidant, antiseptic. (To be distributed in variable proportions according to the viscosity.) pH between 4.5 and 6.5 (preferably citric acid.)

Soluble film
Benzalkonium fluoride: 1.00%
Excipients: polyvinyl alcohol, glycerin, sorbitol, propylene glycol, distilled or purified water, antioxidant. pH between 4.5 and 6.5 (preferably citric acid).

Tablets
Benzalkonium fluoride: 20 mg per tablet
Excipients: lactose, magnesium stearate, cellulose, starch, citric acid, sodium bicarbonate.

Synthetic soaps in bar or paste form
Benzalkonium fluoride: 2%
Excipients: foaming and wetting products that are compatible with quaternary ammonium compounds (for example, amphoteric surfactant of the betaine or aminobetaine type), emollients, stabilizer, antioxidant, antiseptic. pH of between 4.5 and 6.5 (preferably citric acid).

Ready-to-use solutions
Benzalkonium fluoride: 0.40%
Excipients: distilled or purified water, ethanol, antioxidant, glycerin, sorbitol, antiseptic. pH between 4.5 and 6.5 (preferably citric acid).

Solutions to be diluted
Benzalkonium fluoride: 10%
Excipients: distilled or purified water, ethanol, antioxidant, glycerin, sorbitol, antiseptic. pH between 4.5 and 6.5 (preferably citric acid).

The preferred galenical forms combining benzalkonium fluoride with lithium fluoride are as follows:

Cream
Benzalkonium fluoride: 0.80%
LiF: 0.55%
Excipients: emulsive agent, preservative such as KATHON (registered trademark), purified water, perfume qs. 100%.

Jelly: same formulations as the cream
Excipients: soluble derivatives of cellulose, glycerin, preservative such as KATHON (registered trademark), purified water, perfume qs. 100%.

Pad: impregnated with the cream defined above.
Tablets
Benzalkonium fluoride: 0.016 g
LiF: 0.010 g
Excipients: sodium bicarbonate, citric acid, colloidal silica, cellulose, magnesium stearate, lactose qs. 1 tablet.

Soluble sheet: same formulations as the cream
Excipients: polyvinyl alcohol, glycerin, preservative such as KATHON (registered trademark), purified water qs. 100%.

Pessaries
Benzalkonium fluoride: 0.015 g
LiF: 0.010 g
Excipients: semi-synthetic glycerides, preservative such as KATHON (registered trademark) qs. 1 pessary.

APPLICATION OF THE INVENTION IN THE FIELD OF ANTISEPSIS, ANTIBIOTIC THERAPY, ETC., AND, IN PARTICULAR, IN COMBATING STD's

The preferred galenical forms of the invention, for example, for its application in dermatology and venereology by way of an antiseptic are as follows:

Creams and milks
Benzalkonium fluoride: 1.00%
Excipients: distilled or purified water, humectants, emulsifier, stabilizer, antioxidant, antiseptic. (To be distributed in variable proportions according to the viscosity.) pH from 4.5 to 6.5 (preferably citric acid).

Ointments and salves
Benzalkonium fluoride: 1.00%
Excipients: distilled or purified water, emulsifier, excipients of the fatty type (vaseline, lanolin, lanovaseline, stearovaseline), stabilizer, antioxidant, antiseptic. (To be distributed in variable proportions according to the viscosity.) pH from 4.5 to 6.5 (preferably citric acid).

Synthetic soaps in bar or paste form
Benzalkonium fluoride: 1.8 to 2.0%
Excipients: foaming and wetting products that are compatible with quaternary ammonium compounds (for example, amphoteric surfactant of the betaine or aminobetaine type), emollients, stabilizer, antioxidant, antiseptic, citric acid pH regulator.

Solutions
Benzalkonium fluoride: 1.00%
Excipients: distilled or purified water, ethanol, antioxidant, glycerin, sorbitol, antiseptic. pH from 4.5 to 6.5 (preferably citric acid).

The following galenical forms may be (for example, and without implied limitation) used by way of a dermatological local antiseptic (skin, mucosa, etc.):
Foaming bar
Benzalkonium fluoride: 1.8%
LiF: 0.04%
NaF: 1.5%
Excipients: foaming synthetic base, preservative such as KATHON (registered trademark), purified water, perfume qs. 100%.

Foaming paste: same formulations as for the foaming bar, except for the excipient formulated as a paste.
Moisturizing cream
Benzalkonium fluoride: 0.18%
LiF: 0.04%
NaF: 0.8%
Excipients: emulsive agent, moisturizing principle, wheatgerm oil, sweet almond oil, liquid paraffin, preservative such as KATHON (registered trademark), purified water qs. 100%.

The preferred galenical forms of the invention, for example for its application in dermatology by way of a local antibiotic, are as follows:
Solutions
Erythromycin base: 4%
Benzalkonium fluoride: from 0.2% to 0.8%
Excipients: ethyl alcohol, propylene glycol, distilled water.
Gels
Erythromycin base: 4%
Benzalkonium fluoride: from 0.2% to 0.8%
Excipients: ethyl alcohol, hydroxypropylcellulose, distilled water, glycerin.
Salves
Neomycin base: 0.35%
Benzalkonium fluoride: from 0.2% to 0.8%
or Bacitracin: 50,000 IU %
Benzalkonium fluoride: from 0.2% to 0.8%
or Oxytetracycline hydrochloride: 3%
Benzalkonium fluoride: from 0.2% to 0.8%
or Aureomycin hydrochloride: 3%
Benzalkonium fluoride: from 0.2% to 0.8%
Excipients: vaseline, liquid paraffin, lanolin
Cream
Soframycin sulphate: 2.5%
Benzalkonium fluoride: from 0.2% to 0.8%
Excipients: propylene glycol, polyoxyethylene glycol, distilled water.

The preferred embodiments of the invention, for example for its application in otorhinolaryngology, by way of a local antibiotic, are as follows:
Opthalmic ointments
Aureomycin: 1%
Benzalkonium fluoride: from 0.2% to 0.8%
or Oxytetracycline: 0.50%
Benzalkonium fluoride: from 0.2% to 0.5%
Excipients: vaseline, liquid paraffin, lanolin.
Nasal solution
Soframycin sulphate: 1.25%
Benzalkonium fluoride: from 0.50% to 1%
Excipients: distilled water, citric acid, sodium chloride.

APPLICATION OF THE INVENTION IN THE FIELD OF DISINFECTION

This field relates to the treatment of floors, surfaces, instruments, etc., with contact bactericidal products.

The preferred embodiments of the invention for this application are as follows:

| USE | BENZALKONIUM FLUORIDE | EXCIPIENTS |
|---|---|---|
| Hands | 0.05% to 0.1% | purified water or alchohol qs. 100% |
| Epidermis | | |
| Instruments to be sterilized or to be disinfected | 0.08% to 1.0% | purified water qs. 100% |
| Textiles | 0.05% | purified water qs. 100% |
| Instruments of thermometer type | 0.08% to 1.0% | 10% ethanol purified water qs. 100% |
| Washing of surfaces (rooms, boarding, floors) | 0.1% | purified water qs. 100% |

APPLICATION OF THE INVENTION IN COSMETOLOGY

The preferred embodiments of the invention in cosmetology are described below.

The following galenical forms may be presented in cosmetology: creams, milks, salves, solutions, foam baths, synthetic soaps, shampoos, personal hygiene lotions and disinfectant lotions.

The formulae of the excipients are the same as for the pharmaceutical presentations, but the concentrations of benzalkonium fluoride will be different.

These concentrations are as follows: 1.8% to 2% for rinsed products (synthetic soap type) 0.1% to 0.2% for non-rinsed products.

Active principles, chemical or of natural origin, can also participate in these formulations, at concentrations and doses permitted in cosmetology.

The creams and milks can be in an aqueous continuous phase (oil-in-water or water-in-oil emulsion), or pasty in the heated state, to be diluted in water.

The various excipients mentioned by way of example correspond, as a guide and without implied limitation, to the following products:

Humectants: glycerol, propylene glycol, diethylene glycol, polyoxyethylene glycol.

Emulsifiers: sodium stearate, beeswax, sorbitol ester, polyoxyethylene glycol ester, fatty alcohol, triethanolamine-lanolin, Tween, glycol stearate and polyglycols.

Stabilizers: glycol stearate, cetyl alcohol alginate, pectin, gum, polyol fatty esters, soluble esters of cellulose.

Antioxidants: tartaric, citric and ascorbic acids.

Antiseptics: boric acid, benzoic acid, parabenzoic acid and their methyl or propyl esters, in the form of sodium salts or otherwise.

pH: all these formulations are especially effective at pH values between 4.5 and 6.5. To obtain this range, citric acid is mainly used.

We claim:
1. A method for inhibiting or destroying unicellular living organisms of a human or animal, except those present in the dental area of said human or animal, which method comprises contacting the unicellular living organisms with a composition which comprises an effective amount of an effective amount of at least one quaternary ammonium salt of the formula:

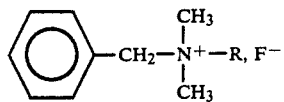

wherein R is an alkyl radical of from $C_8H_{17}$ through $C_{18}H_{37}$.

2. The method according to claim 1, wherein said composition further comprises a metal fluoride.

3. The method according to claim 1, wherein said composition further comprises lithium fluoride.

4. The method according to claim 1, wherein said composition further comprises a preservative.

5. The method according to claim 4, wherein said preservative is KATHON (Registered Trademark).

6. The method according to claim 1, wherein said composition further comprises lithium fluoride and the preservative KATHON (Registered Trademark).

7. The method according to claim 1, wherein said composition further comprises lithium fluoride and a metal fluoride.

8. A method for inhibiting or destroying viruses or retrovirus of a human or animal, except those present in the dental area of said human or animal which method comprises contacting said virus or retroviruses with a composition which comprises an effective amount of at least one quaternary ammonium salt of the formula:

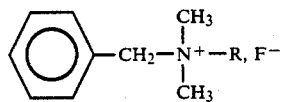

wherein R is an alkyl radical of from $C_8H_{17}$ through $C_{18}H_{37}$.

9. The method according to claim 8, wherein said composition further comprises a metal fluoride.

10. The method according to claim 8, wherein said composition further comprises lithium fluoride.

11. A method according to claim 8, wherein said composition further comprises a preservative.

12. A method according to claim 11, wherein said preservative is KATHON (Registered Trademark).

13. The method according to claim 8, wherein said composition further comprises lithium fluoride and the preservative KATHON (Registered Trademark).

14. The method according to claim 8, wherein said composition further contains lithium fluoride and a metal fluoride.

15. A method for inhibiting or destroying fungi of a human or animal, except those present in the dental area of said human or animal, which method comprises contacting said fungi with a composition which comprises an effective amount of at least one quaternary ammonium salt of the formula:

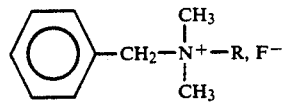

wherein R is an alkyl radical of from $C_8H_{17}$ through $C_{18}H_{37}$.

16. The method according to claim 15, wherein said composition further comprises a metal fluoride.

17. A method according to claim 15, wherein said composition further comprises lithium fluoride.

18. A method according to claim 15, wherein said composition further comprises a preservative.

19. A method according to claim 18, wherein said preservative is KATHON (Registered Trademark).

20. The method according to claim 15, wherein said composition further comprises lithium fluoride and the preservative KATHON (Registered Trademark).

21. The method according to claim 15, wherein said composition further comprises lithium fluoride and a metal fluoride.

22. A method for inhibiting or destroying bacteria of a human or animal except those present in the dental area of the human or animal, which comprises contacting said bacteria with a composition which comprises an effective amount of at least one quaternary ammonium salt of the formula:

$$\text{[benzyl]}-CH_2-\overset{CH_3}{\underset{CH_3}{\overset{|}{N^+}}}-R, F^-$$

wherein R is an alkyl radical of from $C_8H_{17}$ through $C_{18}H_{37}$.

23. The method according to claim 22, wherein said composition further comprises a metal fluoride.

24. The method according to claim 22, wherein said composition further comprises lithium fluoride.

25. The method according to claim 22, wherein said composition further comprises a preservative.

26. The method according to claim 25, wherein said preservative is KATHON (Registered Trademark).

27. The method according to claim 22, wherein said composition further comprises lithium fluoride and the preservative KATHON (Registered Trademark).

28. The method according to claim 22, wherein said composition further comprises lithium fluoride and a metal fluoride.

29. A method for inhibiting or destroying sexually transmissible disease causing organisms which comprises contacting said sexually transmissible disease causing organisms, with a composition which comprises an effective amount of at least one quaternary ammonium salt of formula:

$$\text{[benzyl]}-CH_2-\overset{CH_3}{\underset{CH_3}{\overset{|}{N^+}}}-R, F^-$$

wherein R is an alkyl radical of from $C_8H_{17}$ through $C_{18}H_{37}$.

30. The method according to claim 29, wherein said composition further comprises a metal fluoride.

31. The method according to claim 29, wherein said composition further comprises lithium fluoride.

32. The method according to claim 29, wherein said composition further comprises a preservative.

33. The method according to claim 32, wherein said preservative is KATHON (Registered Trademark).

34. The method according to claim 29, wherein said composition further contains lithium fluoride and the preservative KATHON (Registered Trademark).

35. The method according to claim 29, wherein said composition further contains lithium fluoride and a metal fluoride.

36. A method for inhibiting or destroying spermatozoa which comprises contacting said spermatozoa with a composition which contains an effective amount of at least one quaternary ammonium salt of the formula:

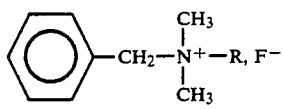

wherein R is an alkyl radical of from $C_8H_{17}$ through $C_{18}H_{37}$.

37. The method according to claim 36, wherein said composition further comprises a metal fluoride.

38. The method according to claim 36, wherein said composition further comprises lithium fluoride.

39. The method according to claim 36, wherein said composition further comprises a preservative.

40. The method according to claim 39, wherein said preservative is KATHON (Registered Trademark).

41. The method according to claim 39, wherein said composition further comprises lithium fluoride and the preservative KATHON (Registered Trademark).

42. The method according to claim 39, wherein said composition further comprises lithium fluoride and a metal fluoride.

43. A method for inhibiting pathogenic microorganisms of a human or animal which comprises contacting said pathogenic microorganisms with an antibiotic composition which comprises an effective amount of an antibiotic agent associated with a quaternary ammonium salt of the formula:

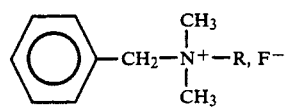

an effective amount of wherein R is an alkyl radical of from $C_8H_{17}$ through $C_{18}H_{37}$.

44. The method according to claim 43 wherein said antibiotic agent is selected from the group consisting of betalactamins, macrolides, polypeptidic antibiotics, phenicolated antibiotics, rifamycins, lincosamides, streptogramines, sulfamides, trimethoprimes, aminosides, cyclins, quinolones and their derivatives and combinations thereof.

* * * * *